(12) United States Patent
Elnajjar

(10) Patent No.: US 10,064,709 B2
(45) Date of Patent: Sep. 4, 2018

(54) SEPARABLE SEGMENTED CASTING RING FOR MAKING INVESTMENT MOLDS

(71) Applicant: Jean J. Elnajjar, Miami, FL (US)

(72) Inventor: Jean J. Elnajjar, Miami, FL (US)

( * ) Notice: Subject to any disclaimer, the term of this patent is extended or adjusted under 35 U.S.C. 154(b) by 0 days.

(21) Appl. No.: 14/181,665

(22) Filed: Feb. 15, 2014

(65) Prior Publication Data

US 2014/0231615 A1    Aug. 21, 2014

Related U.S. Application Data

(60) Provisional application No. 61/765,030, filed on Feb. 15, 2013.

(51) Int. Cl.
*A61C 13/20* (2006.01)

(52) U.S. Cl.
CPC .................................. *A61C 13/20* (2013.01)

(58) Field of Classification Search
CPC ....... A61C 13/20; A61C 13/081; A61C 13/00; B22C 7/005; B22C 9/046; B29C 39/003; B29L 2031/753; B29L 2031/7536
USPC ............... 249/54, 57–59, 95, 139, 154, 160, 249/163–165, 168, 173, 110, 119; 425/175, 176, 179, 180, DIG. 11; 264/16–19; 164/246, 249, DIG. 4, 164/246.249, 376, 374
See application file for complete search history.

(56) References Cited

U.S. PATENT DOCUMENTS

| | | | |
|---|---|---|---|
| 1,970,261 A * | 8/1934 | Turner | 164/376 |
| 1,976,655 A * | 10/1934 | Carpenter | 249/54 |
| 2,450,567 A * | 10/1948 | Schwartz | 164/376 |
| 3,082,496 A * | 3/1963 | Bungeroth et al. | 164/435 |
| 3,217,067 A * | 11/1965 | Tencate | A61C 13/04 264/18 |
| 3,291,437 A * | 12/1966 | Bowden et al. | 249/48 |
| 3,648,760 A * | 3/1972 | Cooper | A61C 13/0003 164/244 |
| 3,724,982 A * | 4/1973 | Davis | 425/117 |
| 3,768,544 A * | 10/1973 | Padeh | 164/376 |
| 4,133,371 A * | 1/1979 | Birch et al. | 164/350 |
| 4,161,208 A | 7/1979 | Cooper | |

(Continued)

FOREIGN PATENT DOCUMENTS

| | | | | |
|---|---|---|---|---|
| JP | 63203323 A * | 8/1988 | | B29C 67/22 |
| JP | 05337595 A * | 12/1993 | | B22C 7/02 |

*Primary Examiner* — Matthew J Daniels
*Assistant Examiner* — Leith S Shafi
(74) *Attorney, Agent, or Firm* — Calrie Marsh, Esq

(57) ABSTRACT

A separable ring apparatus for producing an investment mold is formed of a pair of semi-cylindrical half segments of flexible resilient high temperature resistant material; each having laterally opposed longitudinal sides, an interior with a longitudinal concave semicircular surface of a first smaller radius at opposed ends, and a longitudinal concave semicircular recess of a second larger radius intermediate the opposed ends. Each of the segments has a respective mating joint element extending longitudinally along the opposed longitudinal sides, respectively, for releasably joining the segments together in opposed facing relation to form an elongated generally cylindrical ring having opposed top and bottom ends defining a central circular bore of a smaller diameter at upper and lower ends, and a larger diameter recessed cavity intermediate the upper and lower ends.

11 Claims, 3 Drawing Sheets

(56) References Cited

U.S. PATENT DOCUMENTS

| | | | |
|---|---|---|---|
| 4,307,044 A * | 12/1981 | Perez | 264/19 |
| 4,431,420 A * | 2/1984 | Adair | 106/35 |
| 4,508,155 A | 4/1985 | Rousseau | |
| 4,695,254 A * | 9/1987 | Herrell | 433/213 |
| 4,749,020 A | 6/1988 | Rousseau | |
| 4,777,996 A * | 10/1988 | Finelt | 164/237 |
| 4,825,934 A * | 5/1989 | Kai | 164/361 |
| 4,842,037 A * | 6/1989 | Brown et al. | 164/45 |
| 4,962,909 A * | 10/1990 | Kohler | 249/54 |
| 5,216,863 A * | 6/1993 | Nessa et al. | 52/439 |
| 5,655,592 A * | 8/1997 | Sullivan | 164/456 |
| 5,688,533 A * | 11/1997 | Berger | A61C 13/20 164/237 |
| 5,893,405 A * | 4/1999 | Berger | 164/244 |
| 6,167,669 B1 * | 1/2001 | Lanc | 52/426 |
| 6,220,855 B1 * | 4/2001 | Asheim | 431/294 |
| 6,740,267 B1 * | 5/2004 | Sekino et al. | 264/19 |
| 7,114,547 B2 | 10/2006 | Sullivan et al. | |
| 2002/0125592 A1 * | 9/2002 | Schulman et al. | 264/16 |
| 2005/0115460 A1 * | 6/2005 | Petticrew | 106/35 |
| 2006/0076698 A1 * | 4/2006 | Hamlin | 264/16 |
| 2006/0188837 A1 * | 8/2006 | Helmberger et al. | 433/34 |
| 2008/0072510 A1 * | 3/2008 | Wells et al. | 52/251 |

\* cited by examiner

SEPARABLE SEGMENTED CASTING RING FOR MAKING INVESTMENT MOLDS

CROSS REFERENCE TO RELATED APPLICATION

This application claims priority of U.S. Provisional Application Ser. No. 61/765,030 filed Feb. 15, 2013, the pendency of which is extended until Feb. 18, 2014 under 35 U.S.C. 119(e)(3).

BACKGROUND OF THE INVENTION

1. Field of the Invention

This invention relates generally to casting devices for making investment molds and, more particularly, to a separable segmented casting ring for making investment molds for casting of dental prosthesis.

2. Background Art

As used herein the following terms have the following meanings.

A "casting ring", also known as a "pressing ring" is a hollow, typically cylindrical or oval casing or sleeve that surrounds the wax pattern of the dental appliance to be molded. It is attached to a base known as a "former base" to form a vessel or container into which the investment solution is poured. The investment material then hardens around the wax pattern to form the "investment mold". The present invention is directed to this type of ring.

An "investment mold", also known as an "investment ring" or "mold", is the generally cylindrical or oval ring comprised of the investment material that encases the wax pattern of the dental appliance and which is heated to evacuate the wax and leave a cavity that is an exact negative of the dental appliance to be molded.

In dental practice "investment casting", also known as "precision casting", or the "lost wax" technique, is used to create a casting from a wax pattern that is a duplicate of the object to be cast. The wax pattern is an accurate replica of the shape of a dental appliance. The wax pattern is attached to one or more thin wax sprues. The sprue is attached to a cylindrical or conical sprue former in a base to hold the wax pattern in place. A hollow, typically cylindrical or oval casing or sleeve known as "casting ring" or "pressing ring" is attached to the former base and surrounds the sprues and wax pattern of the dental appliance to be molded and form a vessel or container into which the investment solution is poured. The investment material then hardens around the wax pattern to form the investment mold.

When the base of the sprue former is removed from the investment mold, it leaves a cylindrical or conical shaped cavity in the end of the investment mold with the wax sprue wires extending from the cylindrical or conical shaped cavity into the wax pattern of the dental appliance to be molded.

After the former base has been removed from the investment mold and the casting ring, the casting ring is removed from the mold. In the case of cylindrical rings and molds, this is typically accomplished by manually pressing the mold out of the ring by applying pressure with the thumbs to force the mold out from one end of the ring.

The investment mold is then heated in an oven to melt and burn out the wax, and remove or divest the wax material and cure the mold, leaving a cavity that is an exact negative of the dental appliance to be molded connected by sprue channels to the cylindrical or conical shaped cavity in the end of the investment mold.

In a conventional hot pressing process, the investment mold is inverted and placed in a hot press oven and a disk or ingot of the dental material such as ceramic dental material (generally referred to as a pressable ceramic) that is to be used to form the appliance is placed in the cylindrical or conical shaped cavity in the end of the mold and heated until it is fluid or semi-fluid and is injected under pressure into the cavity of the mold through the sprue channels by means of a pressing plunger.

One of the problems associated with conventional cylindrical casting rings and pressing rings in a standard smaller diameter size is that typically no more than two dental appliances will fit in the interior, otherwise the investment mold will crack when subjected to the piston pressure in the pressing oven because of the small space between the inside diameter of the ring and the outermost dental pattern cavity. Typically, this problem is solved by using a larger diameter ring to form to mold having a greater diameter. However this solution also presents several problems, such as: maintaining an inventory of different size rings; the amount of investment material used, and wasted, is greater; the larger diameter mold requires more heat and pressing time, resulting in production costs; and more time and labor is required to divesting the dental appliance from the mold.

Another problem associated with the conventional mold forming process is that an exothermic reaction occurs during hardening of the investment material into an investment mold. This occurs at several stages: (1) setting, when the investment material hardens into a solid; (2) curing, additional hardening of the investment mold; and (3) during the pressing operation when the molten dental material is pressed into the mold by a plunger. The investment mold has a smaller volume of investment material and a smaller cross sectional area surrounding the wax pattern of the dental appliance and the cavity formed thereby, thus, the location of the greatest heat buildup due to exothermic reaction and stress as the hot dental material is injected under pressure into the cavity of the investment mold occurs in the area surrounding the wax pattern of the dental appliance and the cavity formed thereby.

The heat generated by both setting and curing causes expansion of the investment material which, when constrained by the casting assembly (casting rings and sprue formers), may result in compression on, and distortion of, the wax pattern within the investment material, or cracking of the mold. Cracking of the mold can also occur due to the heat and pressure that occurs during the pressing operation when the molten dental material is pressed into the mold by a plunger.

There are several patents that disclose casting rings of various constructions that attempt to solve problems associated with investment molds for casting of dental prosthesis.

Carpenter, U.S. Pat. No. 1,976,655, discloses an investment adapted to be encompassed by a casting ring and provided with a casting cavity and a sprue leading thereto. The investment is formed at the upper end portion thereof with a gate of flared contour, the base of the gate being disposed axially of the investment and in the form of a concavity opening centrally thereof into the sprue. The portion of the gate above the concavity is formed with a plurality of endless horizontally disposed shoulders inclining downwardly towards the axis of the investment and a plurality of superposed endless risers inclining from their lower ends in a direction away from the axis of the investment and connecting the inner side of an upper shoulder to the outer side of a lower shoulder, the lowermost shoulder merging at its inner side into the upper end of the wall of the concavity, and the uppermost shoulder being positioned at the terminus of the end portion.

Cooper, U.S. Pat. No. 4,161,208 discloses a precision investment casting assembly having a model support consisting of a central upstanding sprue former and outwardly extending tubes to support wax models. The sprue former is held at one end by a resilient base. A somewhat key-hole shaped recess in the base receives a split flask which encircles the support. An elongated pin engages the free edges of the split flask to close it while embedment material is poured around the support. The pin is removed to release the flask from the embedment material after casting. Proper orientation of the support elements is aided by a plurality of keys and keyways.

Rousseau, U.S. Pat. No. 4,508,155 discloses an apparatus for obtaining improved dental castings comprising an expandable investment ring having a removable base. Formed on the top surface of the base, and within the void defined by the ring, is an indexed sprue former. A curved runner bar having an indexed coping is formed at one end thereof in mating relation to the sprue former. The investment ring is defined by a substantially columnar tube open at each end thereof and including a fracture along its entire longitudinal dimension formed along a zig-zag path. The fracture is initially sealed with a wax prior to pouring the investment material, and then as the investment material hardens and releases heat, the entire ring may expand.

Rousseau, U.S. Pat. No. 4,749,020 discloses an apparatus for the preparation of a dental casting from a dental pattern utilizing an exothermic investment material which expands upon curing which comprises a base having a top surface for supporting the dental pattern and a container having a first and a second open end. The container and the base partially enclose the dental pattern when the first open end of the container is disposed upon the top surface of the base. The second end of the container enables the introduction of the exothermic investment material to completely encompass the dental pattern. The container comprises a first and a second container portion with each of the first and second container portions having a first and a second terminating edge. The first and second terminating edges of the first container portion respectively cooperate with the second and first terminating edges of the second container portion for retaining the uncured exothermic investment material within the container. The first and second terminating edges of the first container portion separate from the second and first terminating edges of the second container portion during the expansion of the exothermic investment material upon the exothermic reaction thereof for producing improved accuracy in the dental casting.

Berger, et al., U.S. Pat. No. 5,406,999, discloses a ringless casting oval for making investment molds for precision casting which has an oval casing which fictionally engages an oval base. Anti-rotation tabs of the base extend into anti-rotation slots in the casing, with both casing and base made of flexible plastic material.

Sullivan, et al., U.S. Pat. No. 7,114,547 discloses an apparatus comprising a casting ring and base sized and dimensioned to be coupled together to form a cavity having one or more walls comprising an inner surface of the casting ring, having a bottom comprising an upper surface of the base, and having a form receiving member portion of the base extending into the cavity. This embodiment includes an indicator forming portion sized and positioned to form an indicator on a mold produced by at least partially filling the cavity with investment and allowing the investment to harden. In some instances the casting ring may have a lower segment sized and dimensioned to surround and receive an upper segment of the base to couple the ring and base together, wherein, the casting ring latches onto an outwardly protruding shoulder of the base when the base and casting ring are coupled together.

Helmberger, et al., U.S. Pat. No. 7,507,080, discloses an apparatus for manufacturing muffles for producing dental prosthetic parts comprises a collar divided at least once in the peripheral direction to form a receiving space for an investment material in which at least one pattern for a dental prosthetic part is arranged before the filling with the investment material. At least one pattern holder simultaneously serves as a spacer for an injection plunger passage and a base part closes an open side of the collar. Holding means encompasses the collar to hold the collar together, with the collar being conical with respect to the longitudinal axis thereof at least in one section for simpler manufacture and better handling. The holding means includes at least one ring, in particular a rigid ring, which has a conical inner surface with which it is pushed onto the conical section in the collar.

SUMMARY OF THE INVENTION

The present invention overcomes the aforementioned problems and is distinguished over the prior art in general, and these patents in particular by a separable ring apparatus for producing an investment mold. The ring is formed of a pair of semi-cylindrical half segments formed of soft flexible resilient high temperature resistant material; each having laterally opposed longitudinal sides, an interior with a longitudinal concave semicircular surface of a first smaller radius at opposed ends, and a longitudinal concave semicircular recess of a second larger radius intermediate the opposed ends. Each of the segments has a respective mating joint element extending longitudinally along the opposed longitudinal sides, respectively, for releasably joining the segments together in opposed facing relation to form an elongated generally cylindrical ring having opposed top and bottom ends defining a central circular bore of a smaller diameter at upper and lower ends, and a larger diameter recessed cavity intermediate the upper and lower ends.

The smaller diameter at the lower end is sized to receive a circular surface of a base of a sprue former, and the larger diameter recessed cavity is sufficient length and diameter to surround an upstanding sprue holder of the base of the former, sprue wires extending from the holder, and a wax pattern of a dental appliance to be molded supported on the sprue wires, in circumferential radially spaced relation. The elongated generally cylindrical ring forms a vessel into which investment solution is poured for producing an investment mold having a smaller diameter at upper and lower ends and a larger diameter circumferential ring intermediate the upper and lower ends that surrounds the wax pattern of the dental appliance and the cavity formed thereby.

DESCRIPTION OF THE PREFERRED EMBODIMENT

Figure 1:
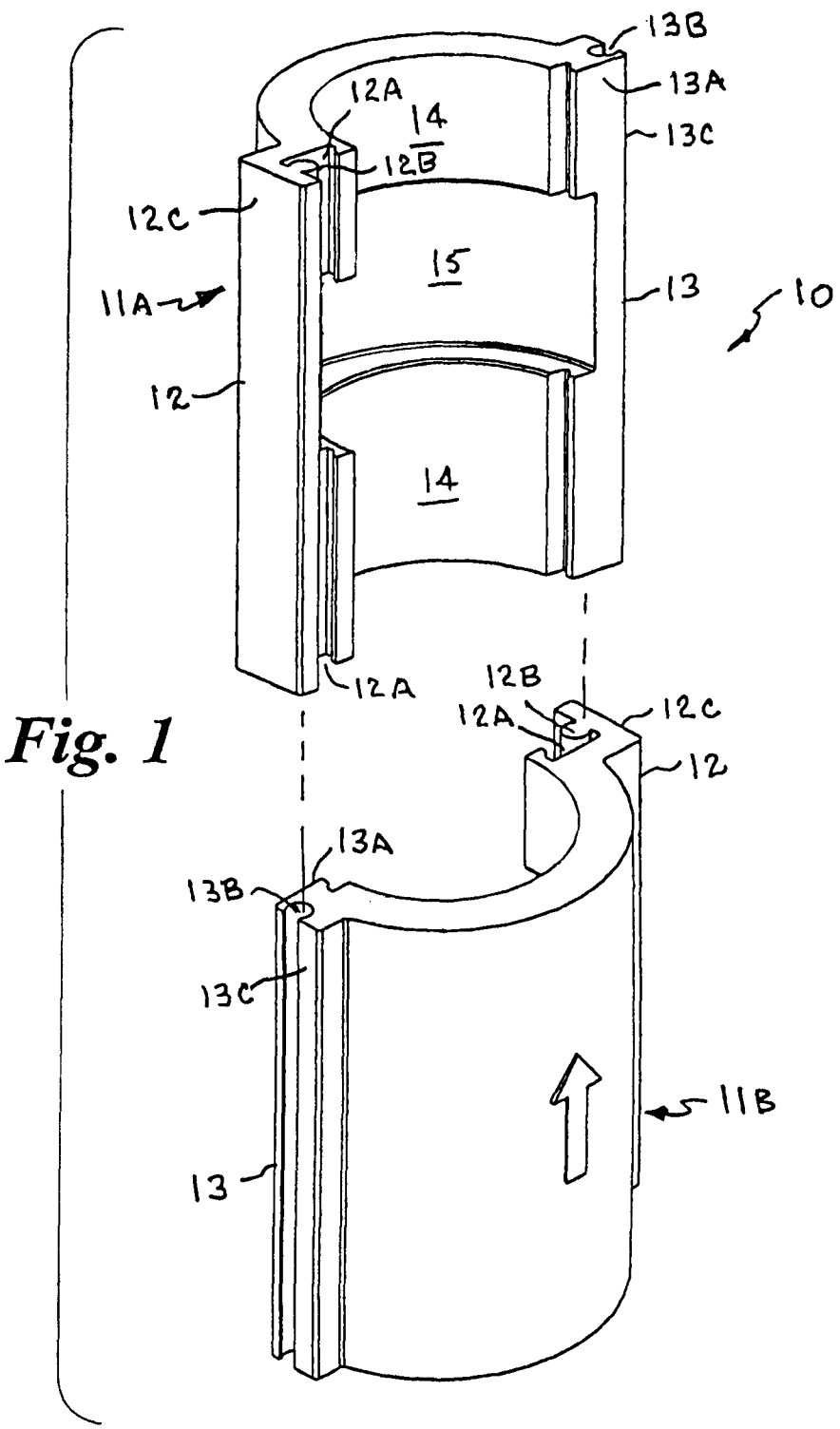
FIG. 1 is an exploded perspective view of the casting ring in accordance with the present invention, showing the two semi-cylindrical segments in an unassembled condition.

Referring to the drawings by numerals of reference, there is shown in FIGS. 1-4, a preferred embodiment of the casting ring 10 of the present invention. The casting ring 10 is comprised of two identical semi-cylindrical half segments 11A and 11B which are slidably assembled together to form the complete ring. The segments are formed of a soft flexible resilient high temperature resistant material such as silicone rubber, for example but not limited thereto. The interior of each segment 11A, 11B has a longitudinal concave semicircular surface 14 of a first smaller radius at opposed ends, and a longitudinal concave semicircular recess 15 of a second larger radius intermediate the opposed ends, as described in more detail hereinafter.

Figure 2:
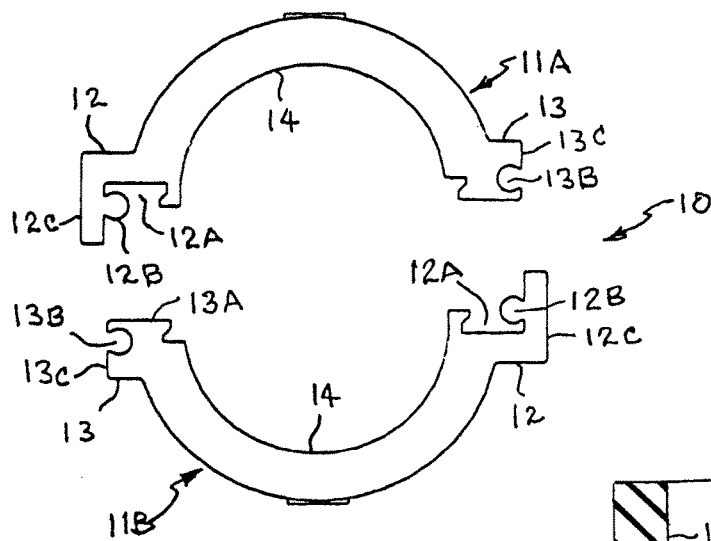
FIG. 2 is a top plan view of the casting ring segments, shown with the two segments in an opposed facing position, to more clearly show the profile of the lateral flanges.
Figure 3:
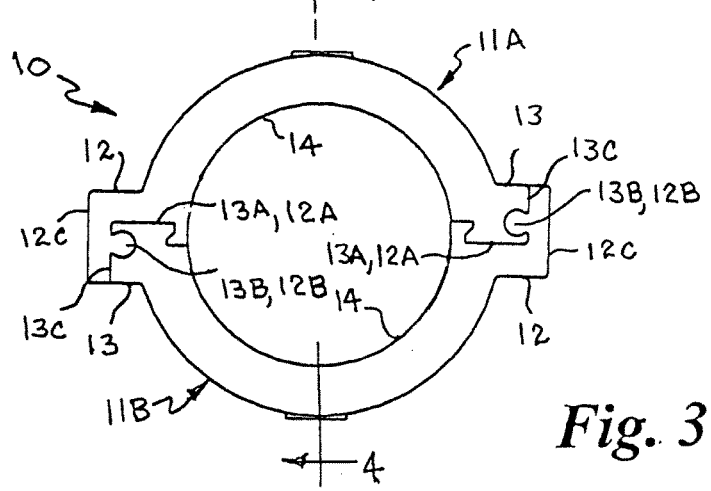
FIG. 3 is a top plan view of the casting ring, shown with the segments in an assembled condition.

As best seen in FIGS. 2 and 3, each half segment 11A, 11B has a first lateral flange 12 and second lateral flange 13, each extending a short distance laterally outwardly from, and longitudinally along, respective opposed sides. Each lateral flange 12, 13, is provided with a longitudinal modified mating tongue and groove and ball and socket configuration.

As seen from the top, the first lateral flange 12 has a recessed generally wedge-shaped cavity 12A with an outwardly rounded bead protrusion 12B facing the cavity 12A. The outer side wall 12C of the first lateral flange 12 extends a short distance beyond the rounded bead protrusion 12B.

The second lateral flange 13 is sized to be slidably received within the first lateral flange 12. The second lateral flange 13 has a generally wedge-shaped tongue protrusion 13A which is sized to be slidably received and removably engaged in the wedge-shaped cavity 12A of the first lateral flange 12, and the outer side wall 13C of the flange is provided with concave inwardly rounded socket 13B which is sized to slidably receive and releasably engage the bead protrusion 12B of the first lateral flange 12.

The two semi-cylindrical segments 11A, 11B, are assembled by positioning them in opposed facing relation with the bottom of the lateral flanges 12, 13, of one segment 11A on the top of lateral flanges 12, 13, of the other segment 11B in longitudinal axial alignment, as shown in FIG. 1, and then manually pressing them together from opposite ends, such that the mating longitudinal modified mating tongue and groove and ball and socket configurations of the lateral flanges become removably engaged.

Figure 4:
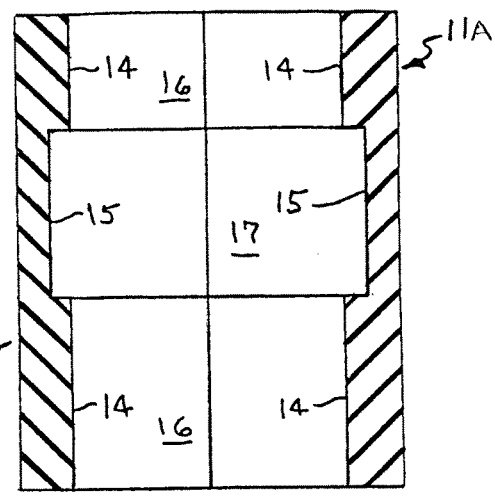
FIG. 4 is a longitudinal cross sectional view of the assembled casting ring taken along line 4-4 of FIG. 3, showing the interior cavity.

As best seen in FIG. 4, when the two segments 11A, 11B are assembled together they form the complete separable ring 10. As mentioned briefly above, the interior of each segment 11A, 11B has a longitudinal concave semicircular surface 14 of a first smaller radius at opposed ends, and a longitudinal concave semicircular recess 15 of a second larger radius intermediate the opposed ends. When the segments are assembled together, the smaller radius longitudinal concave semicircular surfaces 14 define a central circular bore 16 of a smaller diameter at opposed ends, and the larger radius longitudinal concave semicircular recesses 15 define a larger diameter recessed cavity 17 intermediate the opposed ends.

Figure 5:
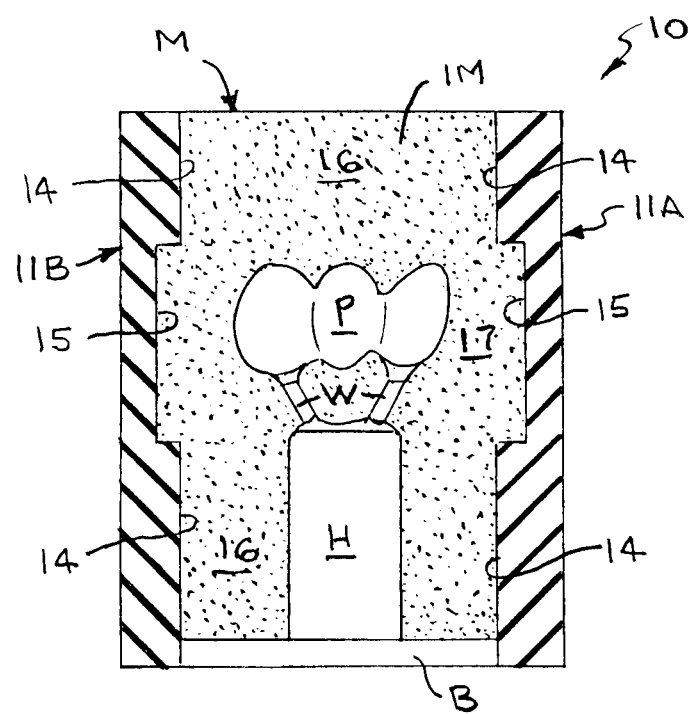
FIG. 5 is a longitudinal cross sectional view of the assembled casting ring similar to FIG. 4, shown surrounding an upstanding sprue holder and wax pattern of the dental appliance and the interior filled with investment material to form the investment mold.

The lower portion of the smaller diameter central circular bore 16 of the assembled ring 10 is sized to receive and frictionally engage the circular surface of the base of a sprue former. As seen in FIG. 5, the larger diameter recessed cavity 17 intermediate the opposed ends or the ring 10 is of sufficient length and diameter to surround the upstanding sprue holder H of the base B, the wax sprue wires W, and the wax pattern P of the dental appliance to be molded, in circumferential radially spaced relation.

As shown in FIG. 5, the upstanding sprue holder H of the base B, is the same or approximate height as the lower portion of the smaller diameter central circular bore 16, whereby the wax sprue wires W, the wax pattern P of the dental appliance to be molded, and the subsequently formed sprue channels, are centered within the longitudinal concave semicircular recess 15 of the second larger radius intermediate the opposed ends 16, and the larger diameter recessed cavity 17 intermediate the opposed ends 16.

Thus, the completed ring 10, when assembled on the base of the sprue former forms a vessel or container into which the investment solution is poured. The investment material IM then hardens around the wax pattern P to form the investment mold M.

After the investment material IM has hardened into the investment mold M, the ring 10 can be removed from the mold and base of the sprue former by manually pulling the segments 11A, 11B apart laterally. The flexibility of the ring material allows the lateral flanges and segment to separate.

When the base of the sprue former is removed from the investment mold, it leaves a cylindrical or conical shaped cavity in the end of the investment mold with the wax sprue wires extending from the cylindrical or conical shaped cavity into the wax pattern of the dental appliance to be molded.

The investment mold is then heated in an oven to melt and burn out the wax, and remove or divest the wax material and cure the mold, leaving a cavity that is an exact negative of the dental appliance to be molded connected by sprue channels to the cylindrical or conical shaped cavity in the end of the investment mold.

In a conventional hot pressing process, the investment mold is inverted and placed in a hot press oven and a disk or pellet of the dental material such as ceramic dental material (generally referred to as a pressable ceramic) that is to be used to form the appliance is placed in the cylindrical or conical shaped cavity in the end of the mold and heated until it is fluid or semi-fluid and is injected under pressure into the cavity of the mold through the sprue channels by means of a pressing plunger.

By forming the investment mold using the present ring, the investment mold has a smaller diameter at opposed ends, and a larger diameter intermediate the opposed ends which is of sufficient length and diameter to surround the cavity that is an exact negative of the dental appliance to be molded and the sprue channels in circumferential radially spaced relation.

Thus, the finished mold has a greater volume of investment material and a larger cross sectional area and wall thickness at the location of the greatest heat buildup that occurs due to the exothermic reaction that takes place as the investment material cures, and at the location that is subject to stress as the hot dental material is injected under pressure into the cavity of the investment mold through the sprue channels by the pressing plunger, and thereby, significantly reducing the likelihood of cracking of the investment mold during those processes.

While the present invention has been disclosed in various preferred forms, the specific embodiments thereof as disclosed and illustrated herein are considered as illustrative only of the principles of the invention and are not to be considered in a limiting sense in interpreting the claims. The claims are intended to include all novel and non-obvious combinations and sub-combinations of the various elements, features, functions, and/or properties disclosed herein. Variations in size, materials, shape, form, function and manner of operation, assembly and use, are deemed readily apparent and obvious to one skilled in the art from this disclosure, and all equivalent relationships to those illustrated in the drawings and described in the specification are intended to be encompassed in the following claims defining the present invention.

The invention claimed is:

1. An apparatus for molding a dental appliance, comprising:
   a separable ring, comprising:
      a pair of semi-cylindrical half segments, each of said half segments having laterally opposed longitudinal sides, an interior with a longitudinal concave semicircular surface of a first smaller radius at opposed ends and a longitudinal concave semicircular recess of a second larger radius intermediate said opposed ends, a first lateral flange and second lateral flange, each extending a short distance laterally outwardly from and longitudinally along respective said opposed longitudinal sides, and mating joint elements each extending longitudinally along said first and second lateral flanges, respectively; and
      each of said half segments releasably joined together in opposed facing relation by pressing them together axially from opposite ends such that said mating joint elements are slidably engaged to form an elongated generally cylindrical ring having opposed top and bottom ends defining a central circular bore of a smaller inside diameter at upper and lower ends thereof, and a larger diameter recessed cavity intermediate said upper and lower ends;
   an investment mold located within said elongated generally cylindrical ring, comprising:
      a first cavity located in an end of the investment mold, at least one sprue channel, and a second cavity, wherein each one sprue channel extends upward from the first cavity and wherein the second cavity extends upward from each sprue channel; and
      wherein the investment mold has a smaller outer diameter at upper and lower ends and a larger diameter circumferential ring intermediate the upper and lower ends;
   wherein said smaller inside diameter of each of the half segments sized to surround a circular surface of the first cavity;
   wherein said larger diameter recessed cavity of each of the half segments circumferentially surrounds the at least one sprue channel and the second cavity of the investment mold;
   wherein said slidably engaged mating joint elements configured to allow removal from the investment mold produced thereby after curing or hardening by pulling said half segments apart laterally to disengage said mating fastener elements; and
   said larger diameter recessed cavity thereby providing a greater volume of investment material of the investment mold and a larger cross sectional area and wall thickness at a location that surrounds wax sprue wires extending from a sprue holder and a wax pattern of the dental appliance to be molded which are supported on the sprue wires, said location being subject to the greatest heat buildup due to the exothermic reaction during curing or hardening of the investment material, which heat buildup contributes to stress and cracking when hot dental material is injected under pressure into the first cavity of the investment mold, wherein the larger diameter recessed cavity is able to withstand the stress and splitting.

2. The apparatus according to claim 1, wherein said mating joint elements extending longitudinally along said first and second lateral flanges comprise a dovetail tongue element protruding outwardly from, and longitudinally along said first lateral flange, and a mating dovetail groove extending longitudinally along said second lateral flange configured to allow removal from the investment mold produced thereby after curing or hardening by pulling said half segments apart.

3. The apparatus according to claim 1, wherein said mating joint elements extending longitudinally along said first and second lateral flanges comprise a bead element protruding outwardly from, and longitudinally along said first lateral flange, and a mating concave socket extending longitudinally along said second lateral flange configured allow removal from the investment mold produced thereby after curing or hardening by pulling said half segments apart.

4. The apparatus according to claim 1, wherein said mating joint elements extending longitudinally along said first and second lateral flanges comprise the combination of a dovetail tongue element and a bead element protruding outwardly from, and longitudinally along said first lateral flange, and the combination of a mating dovetail groove and a concave socket extending longitudinally along said second lateral flange configured to allow removal from the investment mold produced thereby after curing or hardening by pulling said half segments apart.

5. An apparatus for molding a dental appliance, comprising:
   a separable ring, comprising:
      a pair of identical semi-cylindrical segments, each said segment having an upper and lower end and laterally opposing longitudinal sides, each side having a first lateral flange and a second lateral flange located opposite each other, and each lateral flange having both a mating tongue and groove fastening means and a ball and socket fastening means, which fastening means allow the segments to be slidably assembled together to form a cylindrical ring which may be disassembled by pulling apart the lateral flanges;
      each segment having a longitudinal concave interior comprising, a first smaller radius positioned at the upper and lower ends of each segment; and a second larger radius located intermediate the first smaller radius, which second larger radius forms a semicircular recess in each segment; and
      each segment is slidably assembled together to form a cylindrical ring wherein the interior comprises a first smaller diameter positioned at the upper and lower ends of the ring; and a second larger diameter located intermediate the first smaller diameter, which second larger diameter forms a recessed cavity within the center of the ring; an investment mold located within said cylindrical ring, comprising:

a first cavity located in an end of the investment mold, at least one sprue channel, and a second cavity, wherein each one sprue channel extends upward from the first cavity and wherein the second cavity extends upward from the at least one sprue channel; and wherein the investment mold has a smaller outer diameter at upper and lower ends and a larger diameter circumferential ring intermediate the upper and lower ends;

wherein said first smaller radius of each of the half segments sized to surround a circular surface of the first cavity;

wherein said second larger radius of each of the half segments circumferentially surrounds the sprue channels and the second cavity of the investment mold;

the lower end of the cylindrical ring is sized to receive and surround a circular base of a sprue former which base is frictionally engaged with the interior of the ring at the first smaller diameter; and the sprue former extends upward from the circular base, which sprue former having the same height as the first smaller diameter, ending at the point where the recessed cavity begins; and said sprue former has affixed to it and extending from it sprue wires connected to a wax pattern of a dental appliance, and subsequently formed sprue channels, which are all centered within the recessed cavity; and the upper end of the cylindrical ring is open to receive investment material, which is poured into the cylindrical ring sufficient to fill the ring and cover the sprue former, sprue wires, the wax pattern of the dental appliance, and subsequently formed sprue channels; and said investment material is allowed to harden to produce the investment mold which is further subjected to injected pressure, the recessed cavity allows the investment mold to withstand the injected pressure.

6. The apparatus of claim 5, whereby the sprue former accommodates multiple wax patterns of dental appliances, which multiple wax patterns are centered within the recessed cavity of the cylindrical ring.

7. The apparatus of claim 5 wherein the fastening means on each semi-cylindrical segment comprises, a first lateral flange having a recessed wedge-shaped cavity forming a groove with an outwardly rounded bead protrusion facing the cavity; and the outer side wall of the first lateral flange extends out from the rounded bead protrusion; and a second lateral flange having a wedge-shaped tongue protrusion which is sized to slidably receive and releasably engage the groove of the first lateral flange; and the second lateral flange also having outer side wall with a concave inwardly rounded socket which is sized to slidably receive and releasably engage the outwardly rounded bead protrusion of the first lateral flange; and the semi-cylindrical segments are slidably assembled and releasably engaged to form the cylindrical ring, which ring may be manually pulled apart by disengaging the tongue and groove and ball and socket configurations of the first and second lateral flanges.

8. An apparatus for molding a dental appliance, comprising a separable ring, comprising:

two segments which are removably fastened together to form a cylinder, each segment having a longitudinal concave interior comprising, a first smaller radius positioned at the upper and lower ends of each segment; and a second larger radius located intermediate the first smaller radius, which second larger radius forms a semi-circular recessed cavity in each segment;

an investment mold located within the cylinder, comprising:

a first cavity located in an end of the investment mold, at least one sprue channel, and a second cavity, wherein each one sprue channel extends upward from the first cavity and wherein the second cavity extends upward from the at least one sprue channel; and wherein the investment mold has a smaller outer diameter at upper and lower ends and a larger diameter circumferential ring intermediate the upper and lower ends;

wherein said first smaller radius of each of the half segments sized to surround a circular surface of the sprue holder;

wherein said second larger radius of each of the half segments circumferentially surrounds the sprue channels and cavity of the investment mold; and wherein upon hardening of investment material, the segments are detached to uncover the investment mold for molding the dental appliance.

9. The apparatus according to claim 1, wherein the pair of semi-cylindrical half segments are formed of silicone rubber.

10. The apparatus according to claim 5, wherein the pair of identical semi-cylindrical segments are formed of silicone rubber.

11. The apparatus according to claim 8, wherein the two segments are formed of silicone rubber.

* * * * *